(12) United States Patent
Lee

(10) Patent No.: US 11,623,057 B2
(45) Date of Patent: Apr. 11, 2023

(54) CUFF PRESSURE MANAGEMENT DEVICE, A VENTILATOR SYSTEM AND METHOD OF CUFF PRESSURE MANAGEMENT

(71) Applicant: KONINKLIJKE PHILIPS N.V., Eindhoven (NL)

(72) Inventor: Seunghyun Lee, Valrico, FL (US)

(73) Assignee: Koninklijke Philips N.V., Eindhoven (NL)

( * ) Notice: Subject to any disclaimer, the term of this patent is extended or adjusted under 35 U.S.C. 154(b) by 468 days.

(21) Appl. No.: 16/811,575

(22) Filed: Mar. 6, 2020

(65) Prior Publication Data

US 2020/0306473 A1 Oct. 1, 2020

Related U.S. Application Data

(60) Provisional application No. 62/824,516, filed on Mar. 27, 2019.

(51) Int. Cl.
*A61M 16/04* (2006.01)
*A61M 16/00* (2006.01)
(Continued)

(52) U.S. Cl.
CPC ...... *A61M 16/044* (2013.01); *A61M 16/0051* (2013.01); *A61M 16/0057* (2013.01);
(Continued)

(58) Field of Classification Search
CPC .... A16M 16/044; A61M 16/0434–459; A61M 16/022; A61M 16/024; A61M 25/10181–10188
See application file for complete search history.

(56) References Cited

U.S. PATENT DOCUMENTS

2010/0252048 A1\* 10/2010 Young ................ A61M 16/044
128/207.15
2011/0109458 A1 5/2011 Shipman
(Continued)

FOREIGN PATENT DOCUMENTS

JP 2000237314 A 9/2000
WO WO-2013074763 A1 \* 5/2013 ............. A61F 5/445

OTHER PUBLICATIONS

Devys, J.M. et al., "Cuff compliance of pediatric and adult cuffed tracheal tubes: an experimental study". Pediatric Anesthesia 2004, 14: 676-680.
(Continued)

*Primary Examiner* — Philip R Wiest
*Assistant Examiner* — Neil Kauffman
(74) *Attorney, Agent, or Firm* — Daniel H. Brean; Andrew M. Gabriel

(57) ABSTRACT

A cuff pressure management device (10) for a tracheal breathing tube (54) with an inflatable cuff (90), comprises a volume displacement subsystem (36), a pressure transducer (44), a compliance determination circuit (34), and a cuff pressure controller (24). The volume displacement subsystem provides (i) a measured volume of pressurized gas to and from the cuff and (ii) a cuff gas volume signal. The pressure transducer provides a cuff gas pressure signal. The compliance determination circuit is configured to calculate cuff compliance and an estimated tracheal airway compliance based on the gas volume signal and the gas pressure signal. The cuff pressure controller is in controlling communication with the volume displacement subsystem and the compliance determination circuit to maintain cuff pressure based on the calculated cuff compliance.

20 Claims, 7 Drawing Sheets

(51) Int. Cl.
*A61M 16/08* (2006.01)
*A61M 16/20* (2006.01)
*A61M 25/10* (2013.01)

(52) U.S. Cl.
CPC ...... *A61M 16/024* (2017.08); *A61M 16/0875* (2013.01); *A61M 16/209* (2014.02); *A61M 25/10181* (2013.11); *A61M 2016/003* (2013.01); *A61M 2016/0027* (2013.01); *A61M 2205/3344* (2013.01); *A61M 2205/3379* (2013.01); *A61M 2205/581* (2013.01); *A61M 2205/582* (2013.01); *A61M 2205/583* (2013.01); *A61M 2210/1032* (2013.01)

(56) References Cited

U.S. PATENT DOCUMENTS

| | | | |
|---|---|---|---|
| 2011/0178419 A1* | 7/2011 | Wood | A61B 5/08 128/207.14 |
| 2011/0197888 A1 | 8/2011 | Deutsch et al. | |

OTHER PUBLICATIONS

Karasawa, F. et al., "Maintenance of stable cuff pressure in the Brandt™ tracheal tube during anaesthesia with nitrous oxide". British Journal of Anaesthesia 89 (2): 271-6 (2002).

* cited by examiner

CUFF PRESSURE MANAGEMENT DEVICE, A VENTILATOR SYSTEM AND METHOD OF CUFF PRESSURE MANAGEMENT

CROSS-REFERENCE TO RELATED APPLICATIONS

The patent application claims the priority benefit under 35 U.S.C. § 119(e) of U.S. Provisional Application No. 62/824,516 filed on Mar. 27, 2019, the contents of which are herein incorporated by reference.

BACKGROUND

The present embodiments relate generally to tracheal breathing tubes and ventilator systems and more particularly, to a cuff pressure management device, a ventilator system, and a method of cuff pressure management.

In the early days of mechanical ventilation, physicians realized that air was leaking around the endotracheal tube, and didn't inflate the lung properly. They also reported that patients frequently vomited when the tube was inserted past through the gag reflex, causing aspiration pneumonia. A German anesthesiologist, Victor Eisenmenger was recognized as the first physician who adapted an endotracheal tube with a cuff to address these problems.

Two types of tracheal breathing tubes include the endotracheal tube and the tracheostomy tube. Both the endotracheal tube and tracheostomy tube come with a cuff at the distal end or location. The cuff can be inflated by a pilot tube that extends to the proximal end of the tube and terminates with a pilot balloon and spring-loaded valve.

The primary purpose of the cuff is to create a seal between the upper and the lower airway. An effective seal formed by the cuff can prevent contaminated oropharyngeal sections or gastric content from leaking into a sterile lower airway track, which can cause an increased risk of pathogen translocation and ventilator-associated pneumonia (VAP). It also minimizes unintended air leak between a ventilator and a patient, ensuring effective mechanical ventilation.

Despite these clinically significant benefits of cuff seal, an overinflated cuff leads to substantial clinical complications on the tracheal wall, i.e., damages caused by a high cuff pressure. Depending on the degree of blood flow limitation, the adverse effects due to overinflated cuffs can be categorized as lymphatic flow obstruction, venous flow obstruction, and complete stoppage of arterial capillary blow flow and narcosis. But, more commonly, the overinflated cuff results in strider or a sore throat after extubation.

There are four most widely used methods for managing cuff inflation in a clinical setting. The methods include minimal occlusive volume (MOV), minimum leak technique (MLT), cuff pressure measurement (CPM), and manual palpation of the pilot balloon. The MOV technique introduces the least amount of air into the cuff until the air leak during the inspiration stops, thus establishing a cuff seal with minimum cuff pressure.

On the other hand, with MLT a clinician removes air from the cuff until he or she hears a small leak with a stethoscope during the inspiration. The most common method is the CPM, where the intracuff pressure is adjusted between 20 cm $H_2O$ and 30 cm $H_2O$ using a manometer and periodically checked to make sure that the intracuff pressure is maintained within those target pressure ranges and adjust the pressure if needed. The manual palpation method offers a quick and easy assessment of cuff inflation with gentle palpation of the pilot balloon. However, this method is a gross estimate of cuff inflation with high subjectivity and poor repeatability.

A lack of consensus among clinicians about the best approach for monitoring ongoing cuff inflation or the optimum frequency of checking the cuff pressure further creates confusion and notable inconsistency in the cuff management scheme. Many clinical institutions establish a cuff management policy based on trivial knowledge, resource availability, or organizational goals and objectives.

There are several of commercially available devices currently on the market, which attempt to address the cuff management issue: TRACOE smart cuff manager, Python cuff regulator, and Hamilton Intellicuff cuff pressure controller. The TRACOE smart cuff manager controls the intracuff pressure within the pressure range of 20 cm $H_2O$ to 30 cm $H_2O$. It also provides visual verification of an adequate cuff pressure level with a blue buffer balloon, which should be inflated between ⅔ and ¾ of the volume of its outer shell. The TRACOE smart cuff manager is only applicable to use with High Volume Low-Pressure (HVLP) cuffs of tracheostomy and endotracheal tubes. It is not suitable to use with low volume type of cuffs. The Python cuff regulator is a programmable, electronic continuous cuff pressure measurement monitor and management device.

Lastly, the Hamilton IntelliCuff cuff pressure controller is designed to work as either a standalone device or integrated into Hamilton ventilators. Clinicians set the desired cuff pressure between 5 cm $H_2O$ to 50 cm $H_2O$. The IntelliCuff cuff pressure controller automatically controls and maintains the set pressure within a limit. Also, IntelliCuff cuff pressure controller offers safety alarms for disconnection, cuff air leak, and high pressure for intracuff pressure over 50 cm $H_2O$. An automatic deflation feature assists the extubation procedure by bringing the cuff pressure to ambient pressure level.

There are a number of problems and disadvantages with the known devices and methods. Several clinical studies report that a routine manual monitor/control of cuff pressure using a manometer reveals that significant amount of time the cuff pressure is outside of the ideal pressure range (20 cm $H_2O$~30 cm $H_2O$). The existing cuff management systems provide continuous control of the cuff pressure within a target range, which addresses the common pitfall associated with the manual control of cuff pressure using a manometer.

Unfortunately, the efficiency of the constant pressure controller type of the cuff management solution becomes uncertain when what is ideal cuff pressure to create an adequate cuff seal varies significantly among different patients and even with the same patient over time. There are several factors responsible for the changes in the ideal cuff pressures, which are time, positive pressure ventilation, use of nitrous oxide, altitude, measurement of the cuff pressure, muscle relaxation, sedation, hypothermia, different neck and body positions, endotracheal tube positions, duration of intubation, pathologic factors such as laryngeal edema, broncho-constriction, etc.

The use of MOV or MLT to determine the appropriate cuff seal generally results in the cuff pressure being outside of the ideal pressure range (20 cm $H_2O$~30 cm $H_2O$). It is clear that for some patients a much higher cuff pressure (or vice versa, a much lower pressure) is needed to create an adequate seal. However, it is often the case that the cuff pressure is adjusted between 20 cm $H_2O$~30 cm $H_2O$ because several studies demonstrate that MOV and MLT is unreliable with a high inter-subject and intra-subject variability.

A recent effort in modifying the ETT cuff materials with silicon to prevent the micro-channel formation within the inflated cuff and consequent micro-aspiration further complicates the cuff management in the clinical environment with a different recommended cuff pressure. Pneux from Venner recommends an intracuff pressure of 80 cm H$_2$O.

Accordingly, an improved method and apparatus for overcoming the problems in the art is desired.

SUMMARY

In accordance with one aspect, the embodiments of the present disclosure offer a new system and method to manage an endotracheal tube (ETT) or tracheostomy tube cuff. The optimum cuff pressure management system and method automatically identifies and maintains an optimum cuff balloon pressure/volume that is ideal to a given patient's physiological uniqueness. Unlike currently available cuff pressure controller devices where clinicians set an arbitrary cuff pressure target, the optimum cuff pressure management system and method of the present disclosure advantageously identifies the optimum cuff pressure by analysing compliance changes as the cuff balloon inflates through a different anatomical structure of the tracheal airway.

In one embodiment, a cuff pressure management device for a tracheal breathing tube with an inflatable cuff comprises a volume displacement subsystem, a pressure transducer, a compliance determination circuit, and a cuff pressure controller. The volume displacement subsystem provides (i) a measured volume of pressurized gas to and from the cuff and (ii) a cuff gas volume signal. The pressure transducer provides a cuff gas pressure signal. The compliance determination circuit calculates cuff compliance and an estimated tracheal airway compliance based on the gas volume signal and the gas pressure signal. The cuff pressure controller is in controlling communication with the volume displacement subsystem and the compliance determination circuit to maintain cuff pressure based on the calculated cuff compliance.

In one embodiment, the cuff pressure controller is further configured to (i) inflate the cuff, via the volume-displacement subsystem, with increments of the measured volume of pressurized gas, (ii) to acquire simultaneous measurement signals, via the pressure transducer, of intracuff pressure, and (iii) to calculate, via the compliance determination circuit, respective cuff compliances, wherein the compliance determination circuit identifies a predetermined target compliance to an optimum cuff pressure and/or volume as a function of compliance changes in the cuff as the cuff is inflated through different anatomical structures of a given tracheal airway, and wherein the cuff pressure controller subsequently deflates and/or inflates the cuff, via the volume-displacement subsystem, to maintain the predetermined target compliance.

According to another embodiment, the compliance determination circuit is further configured to automatically identify an optimum cuff pressure and/or volume that is ideal to a physiological uniqueness of a given tracheal airway as a function of cuff compliance changes, wherein the optimum cuff pressure and/or volume to create an adequate seal to the physiological uniqueness in the given tracheal airway can vary over time. In one embodiment, the identified optimum cuff pressure and/or volume is selected as a value corresponding to a target range of 50% within +/−5% of an overall compliance change in calculated cuff compliance to the physiological uniqueness of the given tracheal airway. In another embodiment, the identified optimum cuff pressure and/or volume is selected as a value corresponding to a target range between 30% to 50% of an overall compliance change in calculated cuff compliance to the physiological uniqueness of the given tracheal airway.

In a further embodiment, the act of automatically identifying the optimum cuff pressure and/or volume comprises (I) identifying three phases of compliance change that include (i) a first phase in which an increase in compliance starting from a deflated state of the cuff is attributed to compliance of the cuff in a free space corresponding to a tracheal lumen, (ii) a second phase, subsequent to the first phase, in which a further change in compliance of the cuff is attributed to compliance via a direct interaction between the cuff and a tracheal mucosa layer, and a third phase, subsequent to the second phase, in which a still further change in compliance of the cuff is attributed to compliance via the cuff overcoming the tracheal mucosa layer and being impeded by a rigid tracheal cartilage structure, and (II) selecting, in response to identifying an end of the second phase, the optimum cuff pressure and/or volume as a value corresponding to between 30% to 50% of an overall compliance change within the second phase.

According to another embodiment, the calculated cuff compliance includes a change in cuff compliance, wherein the change in cuff compliance is determined by a change in volume of the cuff divided by a corresponding change in cuff pressure. In yet another embodiment, the calculated cuff compliance includes a change in total cuff compliance that comprises three components influenced by an anatomy of a trachea that includes (i) a tracheal lumen, (ii) a tracheal mucosa, and (iii) a tracheal cartilage.

With respect to the three components, a first component comprises a compliance change in the tracheal lumen, $C_{(TL)}$, that corresponds with an actual compliance change of the cuff without any influence by a wall structure of the trachea. A second component comprises a compliance change in the tracheal mucosa, $C_{(TM)}$, that corresponds with an actual compliance change of the cuff with an influence of soft tissue of tracheal mucosa in response to the cuff contacting a surface of the tracheal mucosa. A third component comprises a compliance change in the tracheal cartilage, $C_{(TC)}$, that corresponds with an actual compliance change of the cuff with an influence of tracheal cartilage structure in response to the cuff overcoming the tracheal mucosa layer and becoming impeded by the structure of the tracheal cartilage. Having obtained the three components, the total cuff compliance, $C_{(TOTAL)}$, of the cuff in the tracheal airway is determined according to the equation: $1/(C_{(TOTAL)}) = 1/(C_{(TL)}) + 1/(C_{(TM)}) + 1/(C_{(TC)})$.

According to another embodiment, the volume-displacement subsystem comprises a stepper motor with a fixed cylinder and linear plunger. In another embodiment, the volume-displacement subsystem comprises a centrifugal blower with a flowmeter and a flow control valve. In yet another embodiment, the volume-displacement subsystem is further configured for (i) inflating the cuff for an intubation procedure and (ii) deflating the cuff for an extubation procedure.

In still another embodiment, the compliance determination circuit is further configured to calculate an overall compliance change as a function of the cuff and a given tracheal airway. The default maximum allowable cuff pressure comprises 80% of the overall compliance change. The cuff pressure management device further comprises a pressure relief valve configured to activate, in response to a cuff overpressure condition, for connecting an outlet port of the cuff to atmosphere and dissipating the overpressure condition. In addition, the device further comprises an alarm, wherein the cuff pressure controller is further configured, responsive to an activation of the pressure relief valve, for activating the alarm. The alarm comprises at least one of an auditory, visual, and tactile alarm.

According to yet another embodiment, the cuff pressure management device further comprises an extubation assist feature, wherein the cuff pressure controller is further configured, responsive to an initiation of the extubation assist feature, for precisely deflating, via the volume-displacement subsystem, an entire volume of pressurized gas from the cuff.

In another embodiment, a ventilator system for delivering pressurized gas to a tracheal airway comprises a cuff pressure management device as disclosed in various embodiments herein and a ventilator source of pressurized gas having a pressurized gas output. In one embodiment, the cuff pressure management device further comprises a cuff inflation/deflation connector fluidly coupled to the volume displacement system. In addition, the pressurized gas output of the ventilator source of pressurized gas is configured for being fluidly coupled to a breathing tube, wherein the breathing tube comprises a length of tubing with a ventilator connector at a first proximal end and an atraumatic curved edge at a distal end, wherein the breathing tube further comprises an inflatable cuff proximate the distal end fluidly coupled to a cuff inflating tube, and wherein the cuff inflation/deflation connector is configured to be fluidly coupled with the cuff inflating tube.

According to another embodiment, a method of cuff pressure management for a tracheal breathing tube with an inflatable cuff comprises: providing, via a volume displacement subsystem, (i) a measured volume of pressurized gas to and from the cuff and (ii) a cuff gas volume signal; providing, via a pressure transducer, a cuff gas pressure signal; calculating, via a compliance determination circuit, a cuff compliance and an estimated tracheal airway compliance based on the gas volume signal and the gas pressure signal; and controlling, via a cuff pressure controller in controlling communication with the volume displacement subsystem and the compliance determination circuit, to maintain cuff pressure based on the calculated cuff compliance.

In one embodiment, the method further comprises automatically identifying, via the compliance determination circuit, an optimum cuff pressure and/or volume that is ideal to a physiological uniqueness of a given tracheal airway as a function of cuff compliance changes, wherein the optimum cuff pressure and/or volume to create an adequate seal to the physiological uniqueness in the given tracheal airway can vary over time, further wherein automatically identifying the optimum cuff pressure and/or volume comprises (I) identifying three phases of compliance change that include (i) a first phase in which an increase in compliance starting from a deflated state of the cuff is attributed to compliance of the cuff in a free space corresponding to a tracheal lumen, (ii) a second phase, subsequent to the first phase, in which a further change in compliance of the cuff is attributed to compliance via a direct interaction between the cuff and a tracheal mucosa layer, and a third phase, subsequent to the second phase, in which a still further change in compliance of the cuff is attributed to compliance via the cuff overcoming the tracheal mucosa layer and being impeded by a rigid tracheal cartilage structure, and (II) selecting, in response to identifying an end of the second phase, the optimum cuff pressure and/or volume as a value corresponding to between 30% to 50% of an overall compliance change within the second phase.

According to another embodiment, the calculated cuff compliance includes a change in total cuff compliance that comprises three components influenced by an anatomy of a trachea that includes (i) a tracheal lumen, (ii) a tracheal mucosa, and (iii) a tracheal cartilage. In addition, the method includes wherein a first component comprises a compliance change in the tracheal lumen, $C(_{TL})$, that corresponds with an actual compliance change of the cuff without any influence by a wall structure of the trachea, wherein a second component comprises a compliance change in the tracheal mucosa, $C(_{TM})$, that corresponds with an actual compliance change of the cuff with an influence of soft tissue of tracheal mucosa in response to the cuff contacting a surface of the tracheal mucosa, wherein a third component comprises a compliance change in the tracheal cartilage, $C(_{TC})$, that corresponds with an actual compliance change of the cuff with an influence of tracheal cartilage structure in response to the cuff overcoming the tracheal mucosa layer and becoming impeded by the structure of the tracheal cartilage, and wherein the total cuff compliance, $C(_{TOTAL})$, of the cuff in the tracheal airway is determined according to the equation: $1/(C(_{TOTAL})) = 1/(C(_{TL})) + 1/(C(_{TM})) + 1/(C(_{TC}))$.

As can be understood from this disclosure, the embodiments of the present disclosure provide various advantages over the existing solutions. The advantages include one or more of (i) the device and method automatically finding the ideal cuff pressure or volume, (ii) the device and method automatically adjusting cuff pressure to maintain the ideal cuff seal pressure, (iii) the device and method ensuring optimum pressure to reduce tracheal wall damage, (iv) can be used for various patient types and a wide range of airway diameters, (v) can be used with various types of ETT and/or tracheostomy tube, (vi) an entire volume of air is removed when an extubation assist feature is initiated, (vii) the device and method can be integrated into a ventilator to provide seamless cuff pressure management, and the device can be implemented as a standalone model to enable cuff pressure management for transport and ambulatory application(s).

Still further advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1:
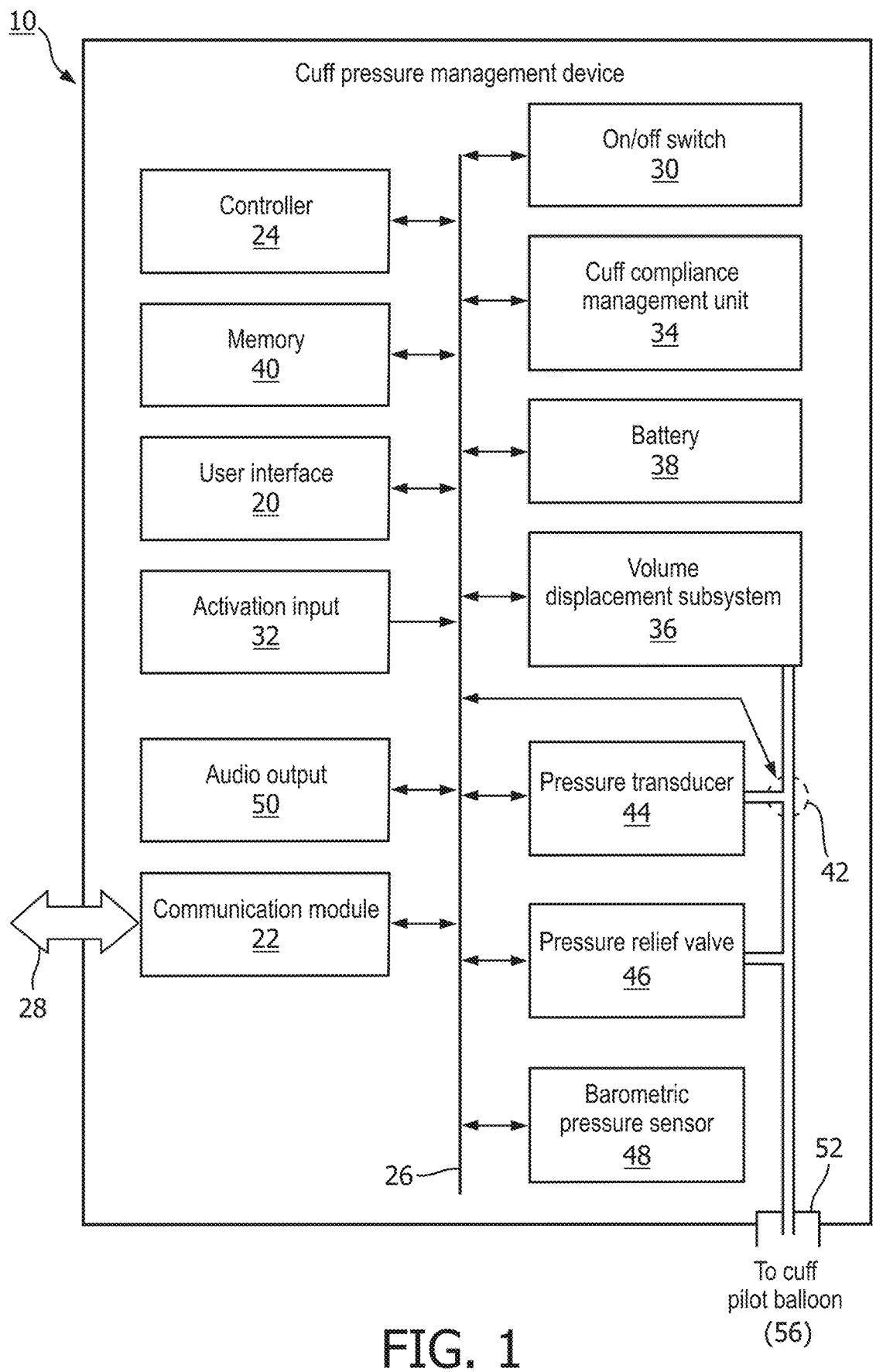
FIG. 1 is a block diagram view of the cuff pressure management device according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

With reference now to FIG. 1, there is shown a block diagram view of the cuff pressure management device 10 according to an embodiment of the present disclosure. The cuff pressure management device 10 can comprise a handheld portable device, for example, for use by a first responder or clinician to carry out at least one action in connection with a subject needing emergency or other treatment according to an embodiment of the present disclosure. In one embodiment, the cuff pressure management device 10 includes at least a user interface 20 and a controller 24. The embodiment may optionally comprise a communications module 22 (or communication means).

The user interface 20 comprises any suitable user interface operatively coupled to at least the controller 24, via signal lines 26, for use in connection with one of an intubation, or an extubation, of a breathing tube equipped with an inflatable cuff, in a tracheal airway as discussed herein. For example, user interface 20 can comprise at least one selected from the group consisting of an input/output device, a tactile output device, a touch screen, an optical display, a microphone, a keypad, a keyboard, a pointing device, an image capture device, a video camera, an audio output device, and any combination thereof, determined as appropriate according to the requirements of a given cuff pressure management device implementation and/or application.

The communications module 22 or communication means is configured for wired or wirelessly communicating, bi-directionally, with at least one communication means (not shown) located within a ventilator (not shown), for example, further within a given immediate proximity of the cuff pressure management device 10. The communications module 22 is further for receiving, via the at least one communication means (now shown) commands and/or data appropriate for a given cuff pressure management implementation. Communications module 22 is preferably a low-power short-range transceiver or wireless or wired connection, which communication is established in response to the at least one communication means (not shown) located within a ventilator (not shown) being disposed in close proximity to the cuff pressure management device. In one embodiment, the communication means or module 22 comprises a communication device configured to communicate via one or more of a passive RFID tag, SPI, Dual SPI, Quad SPI, UART, I2C, Single Wire/1-wire, HSL, Parallel Flash, USB, NFC, RFID, Bluetooth, Fiber optic, Zigbee/ZWAVE, IRDA, and Wi-Fi.

Communication between the communication module 22 of the cuff pressure management device 10 and the at least one communication means (not shown) of the at least one ventilator is indicated by reference numeral 28. In other words, communication between the various devices and components as discussed herein is preferably accomplished using suitable near-field communication techniques known in the art, and thus are not discussed further herein.

The controller 24 operatively couples to the user interface 20 and the communication module 22 via suitable signal lines, indicated via reference numeral 26. Controller 24 is configured for operating in response to at least one of a power up sequence, via ON/OFF switch 30, and/or an activation sequence, via an activation input 32, to perform, via at least a cuff compliance management unit or circuit 34 and a volume displacement subsystem 36, at least one of (i) establishing an optimum cuff seal pressure or volume for an intubation of a tracheal airway with a breathing tube having an inflatable cuff, (ii) automatically adjusting cuff pressure to maintain the ideal cuff seal pressure or volume, (iii) ensuring optimum cuff pressure to reduce tracheal wall damage, and (iv) removing an entire volume of pressurized gas for an extubation sequence, based at least on changes in cuff compliance, as will be discussed further herein.

In one embodiment, controller 24 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given cuff pressure management device implementation and/or application. Controller 24 can further comprise one or more of various modules, units, or subsystems as discussed herein.

With reference still to FIG. 1, the cuff pressure management device 10 further comprises one or more of ON/OFF switch 30, the activation input 32, the cuff compliance management unit or circuit 34, the volume displacement subsystem 36, a battery 38, a memory 40, a 3-way stop cock 42, a pressure transducer 44, a pressure relief valve 46, a barometric pressure sensor 48, and an audio output or module 50. Each of the one or more of ON/OFF switch 30, cuff compliance management unit or circuit 34, volume displacement subsystem 36, battery 38, memory 40, 3-way stop cock 42, pressure transducer 44, pressure relief valve 46, barometric pressure sensor 48, and audio output or module 50 is operatively coupled to at least the controller 24, e.g., via signal lines 26.

The ON/OFF switch 30 comprises any suitable switch for powering the cuff pressure management device 10 between ON and OFF. The cuff compliance management unit or circuit 34 comprises any suitable computer program module or circuit for determining cuff compliance and changes in cuff compliance for a given cuff compliance management implementation and/or application. It is understood that the described module may be computer program module which are rendered in a non-transitory computer-readable medium.

In one embodiment, battery 38 can comprise any suitable power source or power supply for a given cuff pressure management device implementation and/or application. In addition, memory 40 can comprise any suitable memory device, operatively coupled to at least the controller 24, for at least storing information thereto, and further for at least subsequently retrieving the information there from. Memory 40 is preferably a somewhat persistent and very low-power volatile memory, such as flash memory, to which data can be automatically written, stored, and subsequently retrieved for use in a given cuff pressure management device implementation and/or application.

The cuff pressure management device 10 is operable for use with a breathing tube (54, FIG. 3), via a cuff inflation/deflation connector 52 being operatively coupled to a cuff pilot balloon (56, FIG. 3) of the breathing tube. In addition, a ventilator (58, FIG. 3) is operatively coupled via suitable communication link 28 (e.g., a near field communication (NFC), Radio Frequency Identification (RFID), or other suitable short-range communication link) with communication module 20 of the cuff pressure management device 10.

According to a still further embodiment, the cuff pressure management device 10 further comprises a visual indicator and an audio output, e.g., via user interface 20 and audio output 50, in communication with the computer hardware controller 24. In one embodiment, in operation, at least one of the visual indicator and the audio output provide an alarm responsive to a sensed overpressure condition, as will be discussed further herein.

Figure 2:
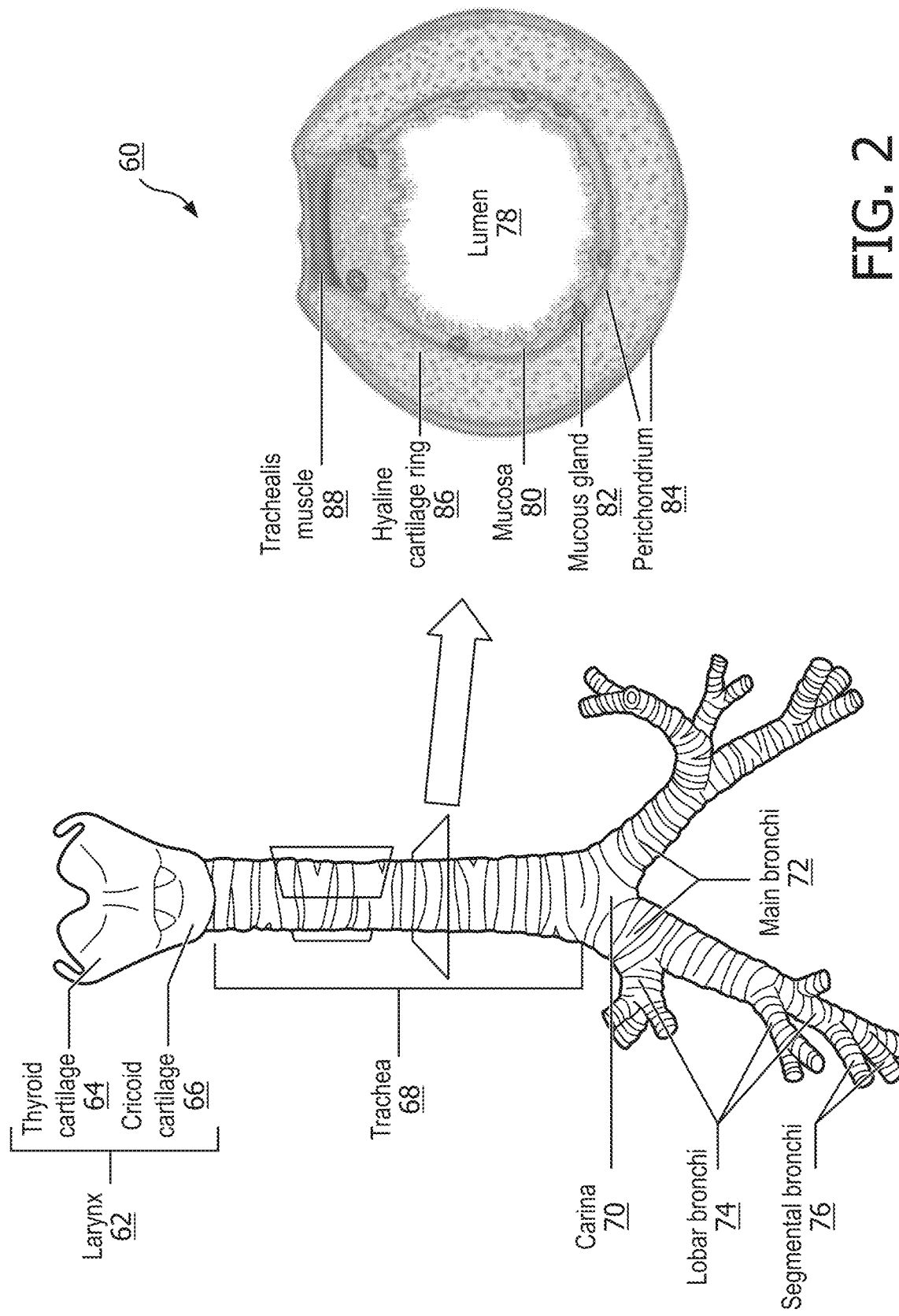
FIG. 2 is an anatomical view of a tracheal anatomy as it relates to the device and method of cuff pressure management according to the embodiments of the present disclosure.

Turning now to FIG. 2, an anatomical view 60 of a tracheal anatomy is shown, as it relates to the device and method of cuff pressure management according to the embodiments of the present disclosure. As will be discussed further herein, a total cuff balloon compliance is made up of three components influenced by the anatomy of the tracheal. The anatomy comprises larynx 62 which includes a thyroid cartilage 64 and a cricold cartilage 66. The anatomy further comprises trachea 68, carina 70, main bronchi 72, lobar bronchi 74 and segmental bronchi 76. FIG. 2 further includes a cross-sectional view of the trachea 68. In the cross-sectional view, the trachea 68 includes a lumen 78, mucosa 80, mucous gland 82, perichondrium 84, hyaline cartilage ring 86, and tracheal muscle 88.

Figure 3:
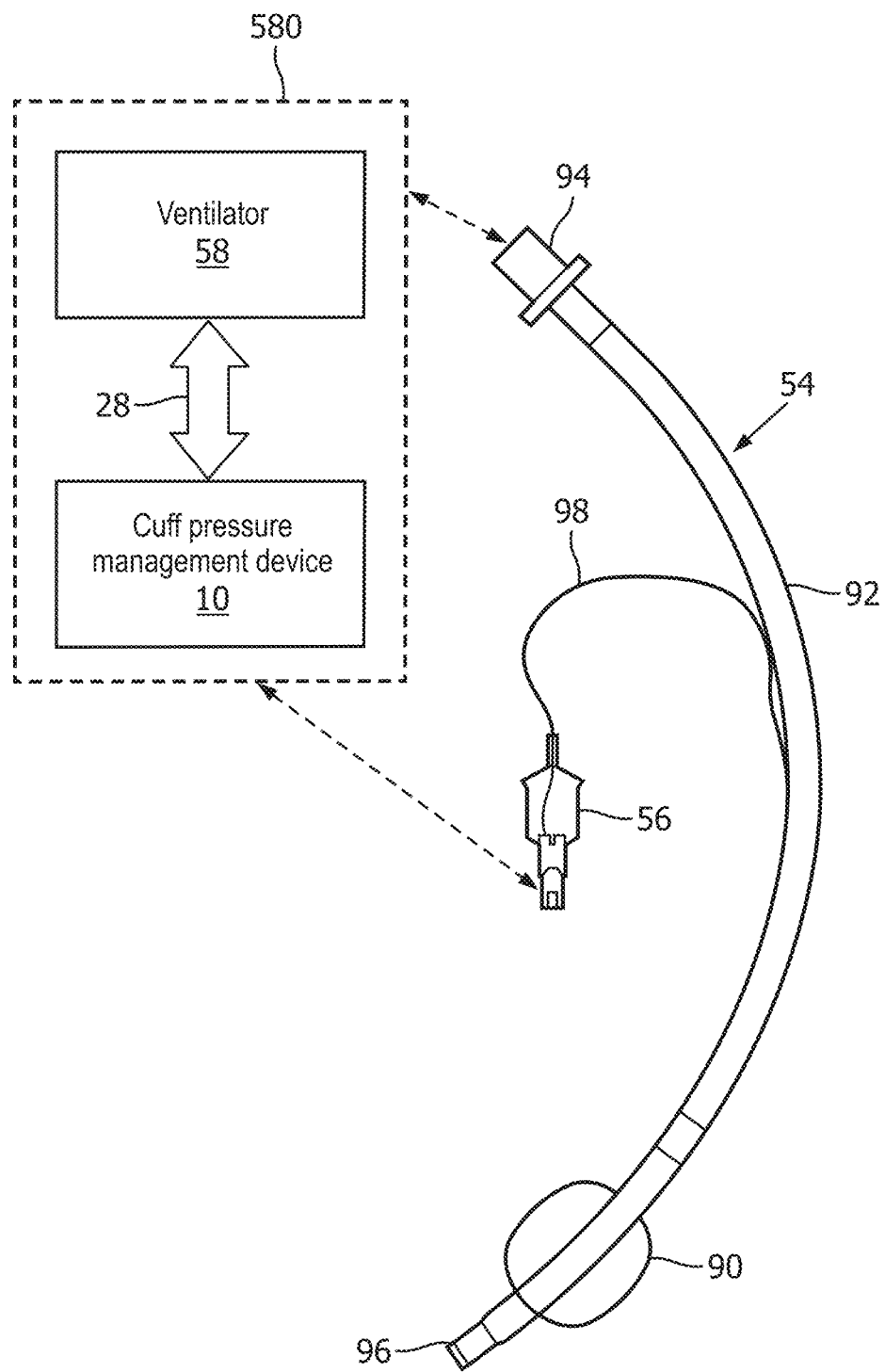
FIG. 3 is a block diagram view of a cuff pressure management device and ventilator operatively coupled to a breathing tube with an inflatable cuff according to various embodiments of the present disclosure.

With reference now to FIG. 3, a block diagram view of a cuff pressure management device 10 and ventilator 58 operatively coupled to a breathing tube 54 with an inflatable cuff 90 according to various embodiments of the present disclosure is shown. The breathing tube 54 comprises a length of tubing 92 with a ventilator connector 94 at a first proximal end and an atraumatic curved edge or beveled tip 96 at a distal end. The breathing tube 54 further comprises the inflatable cuff 90 or cuff balloon overlying and integral with an outer surface of the tubing 92 proximate the distal end. The inflatable cuff is fluidly coupled via a cuff inflating tube 98 to a pilot balloon and spring-loaded one-way valve 56.

As will become apparent from the disclosure herein, the embodiments can include a handheld portable cuff pressure management system 10, or the embodiments may include being integrated into a standalone ventilator (e.g., the integrated embodiment as indicated by the dashed outline 580 in FIG. 3) to provide the ventilator with cuff pressure management capabilities. Other configurations may also be possible.

The design of the cuff pressure management device begins with a precision volume displacement subsystem which can deliver a small volume of pressurized air to the cuff balloon. In one embodiment, a stepper motor with a linear piston can be controlled to produce a known volume of air into the cuff balloon. Simultaneously, a pressure transducer measures the cuff balloon pressure, and the resulting cuff compliance can be calculated as below:

$$\text{Compliance}(C\text{cuff}) = \text{Cuff Volume}/\text{Cuff Pressure}.$$

The volume displacement subsystem can be realized in a couple of different topologies, for example, as follows. In one embodiment, the volume-displacement subsystem (36, FIG. 7) comprises a stepper motor (136, FIG. 7) with a fixed cylinder and linear plunger (138, FIG. 7). In another embodiment, the volume-displacement subsystem comprises a centrifugal blower with a flow measurement system and a flow control valve. Additional configurations of the volume-displacement subsystem may be possible. In addition, the volume-displacement subsystem is further configured for (i) inflating the cuff balloon for intubation and (ii) deflating the cuff balloon for extubation.

An internal one-way pressure relief valve provides a safety mechanism to relieve any unexpected cuff overpressure condition by connecting the cuff balloon via an outlet port to the atmosphere. Upon detection of an overpressure condition, both an audio and visual alarm can be enunciated through an audible alarm and a user interface. Other alarm protocols are contemplated. The integrated barometric pressure sensor (48, FIG. 7) allows freedom of calibration and enhanced mobility; thus, the cuff pressure management device and/or system can be used in various transport situations where altitude change is unavoidable. In addition, in one embodiment, the cuff pressure management device and/or system is completely portable with an integrated rechargeable battery. The battery can be recharged, for example, through a USB port (22, FIG. 7).

The working principle of cuff pressure management device, also referred to herein as the optimum cuff management system (OCMS), relies on identifying compliance changes in the cuff balloon as the cuff balloon is incrementally inflated in known volume increments, over a range of volumes from a first lower volume to a subsequent higher volume, larger than the first volume. Upon completion of each incremental volume of inflation, a cuff pressure is obtained. The incremental cuff compliance, as a function of volume and pressure, is determined through the division of the change in volume of the cuff balloon divided by the corresponding change in the cuff pressure. The total cuff compliance can be made of three components influenced by the anatomy of the trachea: tracheal lumen, tracheal mucosa, and tracheal cartilage.

Compliance in the tracheal lumen ($C_{TL}$) is equal to the cuff balloon compliance in the tracheal lumen, which is the actual compliance of the cuff balloon without any influence by the tracheal wall structure. Compliance in the tracheal lumen can be designated from the time an ETT with a completely deflated cuff is inserted to the tracheal lumen until the inflated cuff outside diameter starts to make, or first starts making, contact with the tracheal epithelium and conforming to its shape. The actual compliance of the cuff balloon without any influence by the tracheal wall structure may optionally be determined prior to insertion or use, or may otherwise be previously known.

Compliance in the tracheal mucosa ($C_{TM}$) is equal to the cuff balloon compliance in tracheal mucosa, which is the actual compliance of soft tissue of tracheal mucosa when the cuff balloon starts and continues to make contact the surface of the tracheal mucosa.

Compliance in tracheal cartilage ($C_{TC}$) is equal to the cuff balloon compliance in tracheal cartilage, which is the actual compliance of the tracheal cartilage rings when the cuff balloon overcomes the tracheal mucosa layers and is impeded by the much more rigid tracheal cartilage structure.

The total compliance of the cuff balloon in the trachea ($C_{TOTAL}$) may be calculated with the following formula:

$$1/(C_{TOTAL})) = 1/(C_{TL})) + 1/(C_{TM})) + 1/(C_{TC})).$$

In addition, derivative parameters to the compliance measurement are also contemplated. Such derivative parameters could be used to determine changes in the rigidity of the tracheal wall structure. For example, derivative parameters may include elastance and a time constant. The elastance is simply inverse of compliance. The time constant is typically used to describe the time required to reach a steady state, which is described by the product of airway resistance and lung compliance in the context of lung mechanics. Since the normal airway resistance is replaced by a fixed diameter ETT, the airway resistance becomes a constant. Thus, the resulting time constant is proportional to the compliance.

Figure 4:
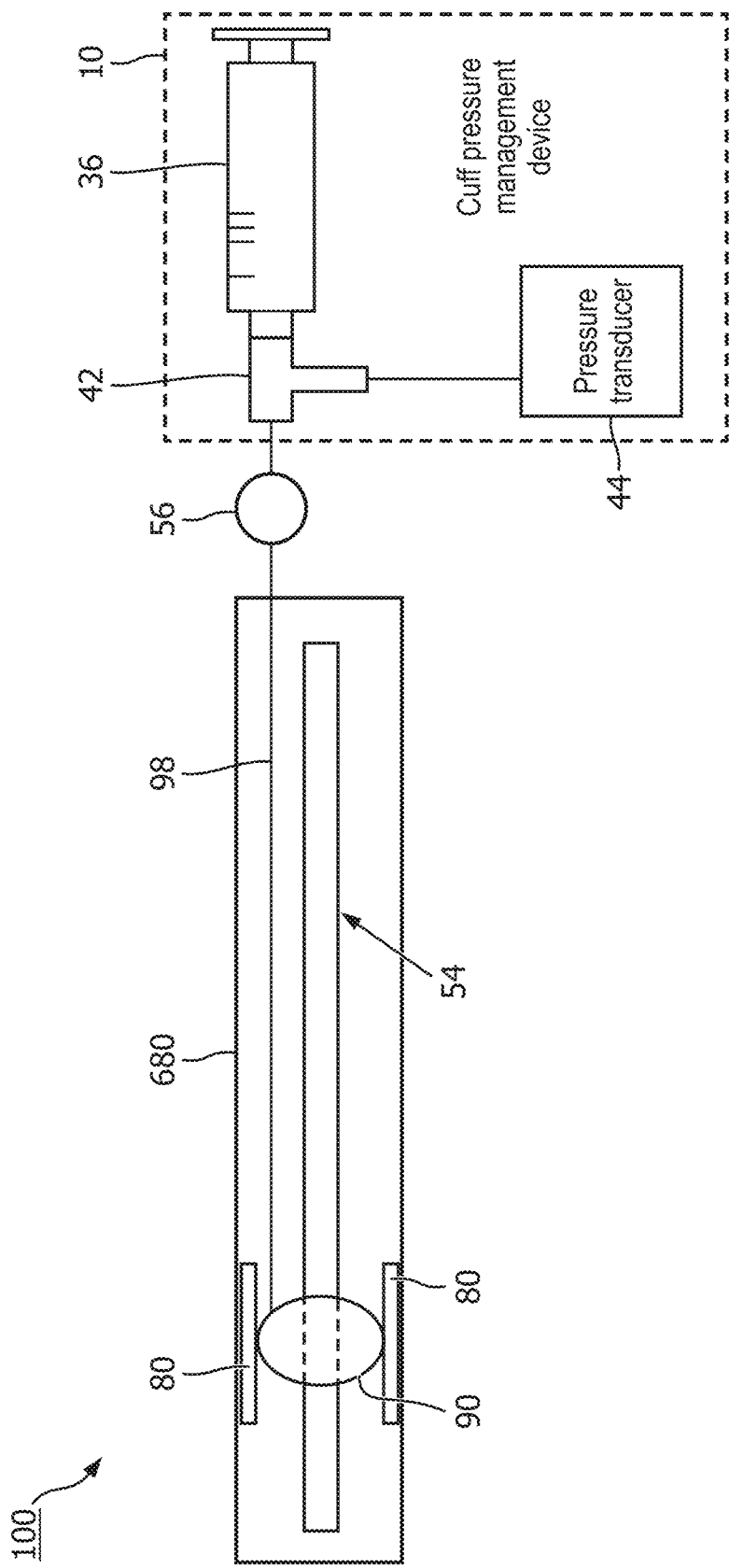
FIG. 4 is an illustrative block diagram view of an in-vitro test setup for a cuff pressure management device according to an embodiment of the present disclosure.

Turning now to FIG. 4, an illustrative block diagram view of an in-vitro test setup 100 for a cuff pressure management device 10 according to an embodiment of the present disclosure is shown. The aim of the in-vitro study was to identify an ideal cuff pressure or cuff volume based on analysing changes in compliance curve within a PVC tracheal model 680. The PVC tracheal model 680 comprises a piece of PVC tubing twenty-two (22) mm in inner diameter and fifteen (15) cm in length. A five (5) mm thick silicon tape was adhered to the inside of the PVC tracheal model 680 as a tracheal mucosa layer 80. A 7.00 mm ID Ruschelt Safety Clear Plus (Teleflex, PA) was used for the endotracheal tube (ETT) 54. A ten (10) ml lure lock syringe with plunger (i.e., used as a volume displacement subsystem) was connected to the pilot balloon 56 of EET 54 and a pressure transducer 44 (Dwyer Instrument, IN) via a three-way stock cock 42.

Figure 5:
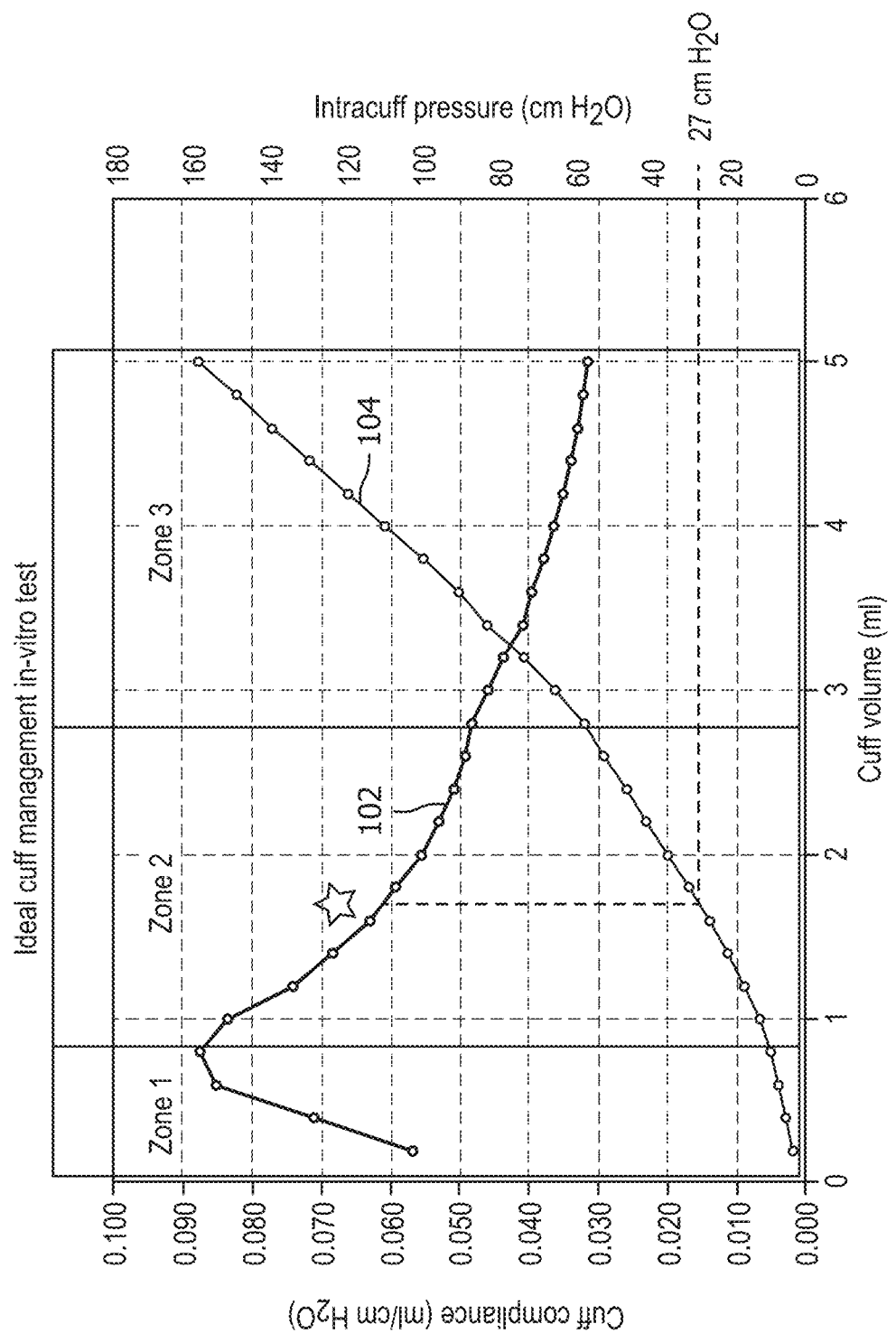
FIG. 5 is a graphical representation view of an example of cuff pressure management device pressure-volume and compliance graphs, plotted overlying one another, according to an embodiment of the present disclosure.

With reference now to FIGS. 3, 4 and 5, initially, the cuff 90 is inflated (e.g., via a precision volume displacement mechanism or subsystem) with increments (e.g., 2 ml increments) of air until the cuff pressure starts to rise above the atmospheric pressure. The first phase is described as "Zone 1" in FIG. 5 (which shows an example of cuff pressure management device pressure-volume and compliance graphs, plotted overlying one another), where the compliance of the cuff balloon increases, attributed by the compliance of the cuff balloon in a free space, i.e., the tracheal lumen (78, FIG. 2). In FIG. 5, the compliance-volume curve is indicated via reference number 102 and the pressure-volume curve is indicated via reference numeral 104. In "Zone 2" (FIG. 5), the compliance is dictated by the direct interaction between the cuff balloon 90 and the tracheal mucosa layer 80. There are noticeable changes in compliance in "Zone 3" (FIG. 5), where the cuff balloon 90 overcomes the tracheal mucosa layer 80 and impeded by the rigid tracheal cartilage structure 86 (FIG. 2). The embodiments of the present disclosure make use of compliance calculations and compliance curve analysis (e.g., manual, slope change, advanced waveform analysis, etc.).

With reference still to FIG. 5, the ideal cuff pressure or volume can be identified in Zone 2. The beginning of Zone 2 is indicated by the compliance change compared to Zone 1, where the cuff balloon starts to press against the mucosa layer, and begin to create a seal around the ETT within the tracheal airway. The ideal cuff pressure or volume can be achieved when sufficient pressure is reached to form a seal, but not overpressure which can result in damage to the mucosa layer. The inventor has determined that between 30%~50% of the compliance change would be a good target as an ideal cuff pressure or volume. With the target compliance change of 50% (e.g., as indicated by the 5-point star in FIG. 5), the in-vitro test result yielded an intracuff pressure of 27 cm $H_2O$ as the ideal cuff pressure for the anatomy of the given PVC tracheal model 680 (i.e., tracheal airway).

In operation, the cuff pressure management device can be used as follows. Once the ETT or tracheostomy tube is correctly inserted in a patient's airway, the cuff pressure management device 10 is connected to the pilot balloon through a bacterial filter (not shown). In one embodiment, the default target compliance change is 50% within +/−5%, however, a clinician or device operator can manually change, via the user interface, the target compliance change setting. Once initiated, the cuff pressure management device 10 automatically inflates the cuff balloon 90 with air volume in desired increments (e.g., 1 ml increments or other suitable increments). The cuff pressure management device 10 continues to inflate the cuff balloon 90 and to monitor, via the pressure transducer 44, the resulting cuff pressure changes until the end of Zone 2 is identified (see FIG. 5), and the ideal cuff target pressure is determined. The cuff pressure management device 10 thereafter starts to deflate the cuff balloon 90 to reach the ideal cuff pressure and provides continuous maintenance of the ideal cuff pressure within the desired target range. The target ideal cuff pressure and the minimum and maximum values are displayed, for example, on the user interface or screen.

In one embodiment, the default maximum allowable cuff pressure is 80% compliance in Zone 2 (FIG. 5), but a clinician can manually set, via the user interface, the maximum cuff pressure limit. If an unexpected overpressure condition occurs (e.g., a cough or upper airway spasm), the pressure relief valve 46 (FIG. 1) activates to alleviate the overpressure condition. In the event of a cuff failure, the cuff pressure management device generates an alarm (e.g., via user interface 20 and/or audio output 50 of FIG. 1).

In another embodiment, when a clinician initiates an extubation assist feature, e.g., via the user interface 20 (FIG. 1), the cuff pressure management device 10 precisely removes, via the volume displacement subsystem 36 (FIG.

1), the entire air volume from the cuff balloon 90 (FIG. 3) to aid an extubation procedure.

Figure 6:
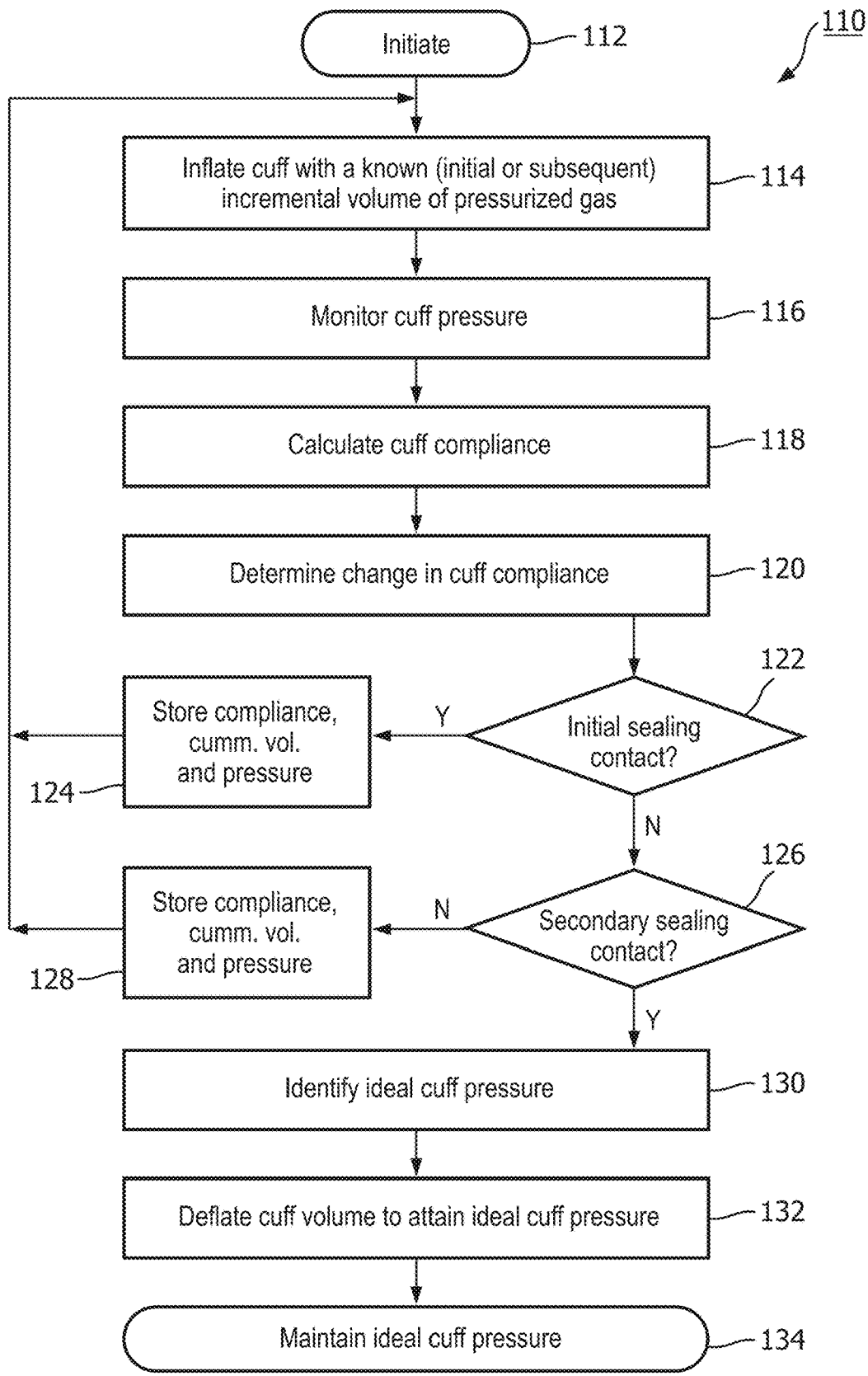
FIG. 6 is a flowchart view of a method for cuff pressure management according to another embodiment of the present disclosure.

With reference now to FIG. 6, a method 110 for cuff pressure management according to another embodiment of the present disclosure will now be discussed. Assuming that the breathing tube with inflatable cuff (in its deflated state) has been properly inserted into a tracheal airway, the method starts at Step 112 with an initiation, e.g., via the activation input 32 (FIG. 1). Optionally, Step 112 begins prior to insertion, wherein the cuff is either inflated to determine a cuff balloon-only compliance, or the cuff balloon compliance is otherwise already known. In this optional sub-step, the cuff is inserted into the tracheal airway after the initiation. At Step 114, the cuff is inflated with a known incremental volume of pressurized gas. The first occurrence of inflating the cuff with the known incremental volume of pressurized gas is referred to as the initial incremental volume of pressurized gas. At Step 116, an intracuff pressure is monitored, via the pressure transducer 44. At Step 118, cuff compliance is calculated, via the cuff compliance management unit or circuit 34. The method then proceeds to Step 120 with a determination, via the cuff compliance management unit or circuit 34, of a change in cuff compliance. At Step 122, a query is performed as to whether the current change in cuff compliance represents an initial sealing contact between the cuff and the mucosa layer that has occurred, based upon a given compliance change indicative of a transition from Zone 1 to Zone 2. If the query determines yes, that the current change in cuff compliance represents an initial sealing contact, then the method proceeds to Step 124. At Step 124, the compliance, cumulative volume of pressurized gas, and the pressure at the initial sealing contact are stored in memory, wherein the data stored in the memory is indicative of the start of Zone 2. The method then repeats back again beginning at Step 114, wherein the cuff is continued to be inflated with a known incremental volume of pressurized gas. The subsequent occurrence of inflating the cuff with the known incremental volume of pressurized gas is referred to as a subsequent incremental volume of pressurized gas. On the other hand, if the result of the query in Step 122 is no, then the method proceeds to Step 126.

At Step 126, a second query is performed as to whether the current change in cuff compliance represents a secondary sealing contact between the mucosa layer and the cartilage that has occurred, based upon a given compliance change indicative of a transition from Zone 2 to Zone 3. If the result of the query at Step 126 is no, indicating that the current change in cuff compliance does not represent the secondary sealing contact, then the method proceeds to Step 128. At Step 128, the current compliance, cumulative volume of pressurized gas, and the pressure are stored in memory, wherein the data stored in the memory is indicative of data either belonging in Zone 1 or Zone 2. The method then repeats back again beginning at Step 114.

On the other hand, if the result of the query at Step 126 is yes, indicating that the current change in cuff compliance represents the secondary sealing contact, then the method proceeds to Step 130. At Step 130, the current compliance, cumulative volume of pressurized gas, and the pressure at the secondary sealing contact are used, in addition to the values of compliance, cumulative volume of pressurized gas, and the pressure at the initial sealing contact that were stored in memory, to identify the start and end, respectively, of Zone 2. The ideal cuff pressure is then identified from within Zone 2, as previously discussed further herein. The method proceeds to Step 132, where the cuff volume is deflated by a given amount to attain the identified ideal cuff pressure. The absolute value of the given amount by which the cuff is to be deflated would correspond to value of the pressure at the end of Zone 2 minus the value of the ideal cuff pressure. Subsequent to attaining the ideal cuff pressure, the ideal cuff pressure is thereafter maintained at Step 134.

In another embodiment, the method of cuff pressure management for a tracheal breathing tube with an inflatable cuff comprises: providing, via a volume displacement subsystem, (i) a measured volume of pressurized gas to and from the cuff and (ii) a cuff gas volume signal; providing, via a pressure transducer, a cuff gas pressure signal; calculating, via a compliance determination circuit, a cuff compliance and an estimated tracheal airway compliance based on the gas volume signal and the gas pressure signal; and controlling, via a cuff pressure controller in controlling communication with the volume displacement subsystem and the compliance determination circuit, to maintain cuff pressure based on the calculated cuff compliance.

In one embodiment, the method further comprises automatically identifying, via the compliance determination circuit, an optimum cuff pressure and/or volume that is ideal to a physiological uniqueness of a given tracheal airway as a function of cuff compliance changes, wherein the optimum cuff pressure and/or volume to create an adequate seal to the physiological uniqueness in the given tracheal airway can vary over time, further wherein automatically identifying the optimum cuff pressure and/or volume comprises (I) identifying three phases of compliance change that include (i) a first phase in which an increase in compliance starting from a deflated state of the cuff is attributed to compliance of the cuff in a free space corresponding to a tracheal lumen, (ii) a second phase, subsequent to the first phase, in which a further change in compliance of the cuff is attributed to compliance via a direct interaction between the cuff and a tracheal mucosa layer, and a third phase, subsequent to the second phase, in which a still further change in compliance of the cuff is attributed to compliance via the cuff overcoming the tracheal mucosa layer and being impeded by a rigid tracheal cartilage structure, and (II) selecting, in response to identifying an end of the second phase, the optimum cuff pressure and/or volume as a value corresponding to between 30% to 50% of an overall compliance change within the second phase.

According to one embodiment, the calculated cuff compliance includes a change in total cuff compliance that comprises three components influenced by an anatomy of a trachea that includes (i) a tracheal lumen, (ii) a tracheal mucosa, and (iii) a tracheal cartilage. In addition, the method includes wherein a first component comprises a compliance change in the tracheal lumen, $C_{(TL)}$, that corresponds with an actual compliance change of the cuff without any influence by a wall structure of the trachea, wherein a second component comprises a compliance change in the tracheal mucosa, $C_{(TM)}$, that corresponds with an actual compliance change of the cuff with an influence of soft tissue of tracheal mucosa in response to the cuff contacting a surface of the tracheal mucosa, wherein a third component comprises a compliance change in the tracheal cartilage, $C_{(TC)}$, that corresponds with an actual compliance change of the cuff with an influence of tracheal cartilage structure in response to the cuff overcoming the tracheal mucosa layer and becoming impeded by the structure of the tracheal cartilage, and wherein the total cuff compliance, $C_{(TOTAL)}$, of the cuff in the tracheal airway is determined according to the equation:

$$1/(C_{(TOTAL)}) = 1/(C_{(TL)}) + 1/(C_{(TM)}) + 1/(C_{(TC)}).$$

Figure 7:
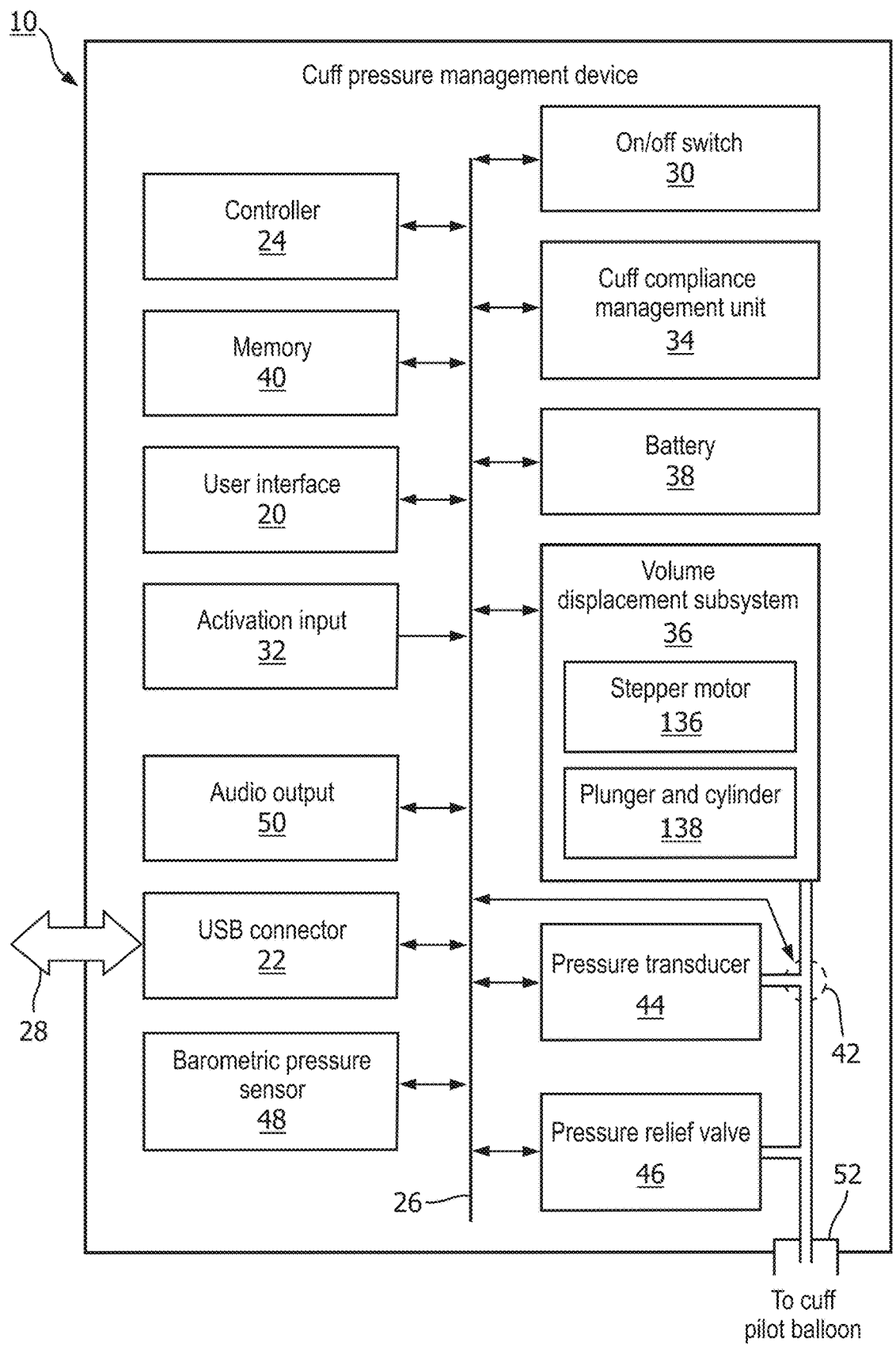
FIG. 7 is a block diagram view of a cuff pressure management device according to another embodiment of the present disclosure.

With reference now to FIG. 7, a cuff pressure management device according to another embodiment of the present disclosure will be discussed. The cuff pressure management device of FIG. 7 is similar to that of FIG. 1, with the following differences. The volume displacement subsystem 36 comprises a stepper motor 136 and a plunger and cylinder 138 for providing a precision volume displacement mechanism that delivers pressurized gas in known increments of pressurized gas (e.g., 1 ml, 2 ml, or other increment). The plunger dispenses a known (incremental and/or total) volume of gas via activation of the plunger in the cylinder by the stepper motor. The amount of dispensed volume would be known via the stepper motor position of the linear plunger. The volume-displacement subsystem could thus output a position signal that would act like a form of flow and/or volume signal. In addition, the communication module 22 comprises a USB port or connector, wherein in addition to data transfer, the USB port or connector provides a way for the battery 38 to be recharged, i.e., through the USB port.

In one embodiment, the various modules described herein can comprise one or more of an integrated circuit, discrete analog or digital circuit components, hardware, software, firmware, or any combination thereof, for performing various functions as discussed herein, further according to the requirements of a given cuff pressure management implementation and/or application. In addition, one or more of the modules can further comprise various combinations of one or more of the various modules.

In another embodiment, the controller described herein comprises one or more microprocessor, microcontroller, field programmable gate array (FPGA), integrated circuit, discrete analog or digital circuit components, hardware, software, firmware, or any combination thereof, for performing various functions as discussed herein, further according to the requirements of a given cuff pressure management device implementation and/or application. The controller can further comprise one or more various modules as discussed herein.

It is understood that the various described modules may be computer program modules which are rendered in a non-transitory computer-readable medium.

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A cuff pressure management device (10) for a tracheal breathing tube (54) with an inflatable cuff (90), comprising:
  a volume displacement subsystem (36) for providing (i) a measured volume of pressurized gas to and from the cuff and (ii) a cuff gas volume signal;
  a pressure transducer (44) for providing a cuff gas pressure signal;
  a compliance determination circuit (34) configured to calculate a cuff compliance based on the gas volume signal and the gas pressure signal and to determine a tracheal airway compliance zone based on the calculated cuff compliance; and
  a cuff pressure controller (24) in controlling communication with the volume displacement subsystem and the compliance determination circuit to maintain cuff pressure based on the calculated cuff compliance and the tracheal airway compliance zone.

2. The device of claim 1, wherein the cuff pressure controller (24) is further configured to (i) inflate the cuff (90), via the volume-displacement subsystem (36), with increments of the measured volume of pressurized gas, (ii) to acquire simultaneous measurement signals, via the pressure transducer (44), of intracuff pressure, and (iii) to calculate, via the compliance determination circuit (34), respective cuff compliances, wherein the compliance determination circuit identifies a predetermined target compliance to an optimum cuff pressure and/or volume as a function of compliance changes in the cuff as the cuff is inflated through different anatomical structures of a given tracheal airway, and wherein the cuff pressure controller subsequently deflates and/or inflates the cuff, via the volume-displacement subsystem, to maintain the predetermined target compliance.

3. The device of claim 1, wherein the compliance determination circuit (34) is further configured to automatically identify an optimum cuff pressure and/or volume that is ideal to a physiological uniqueness of a given tracheal airway as a function of cuff compliance changes, wherein the optimum cuff pressure and/or volume to create an adequate seal to the physiological uniqueness in the given tracheal airway varies over time.

4. The device of claim 3, wherein the identified optimum cuff pressure and/or volume is selected as a value corresponding to a target range of 50% within +/−5% of an overall compliance change in calculated cuff compliance to the physiological uniqueness of the given tracheal airway.

5. The device of claim 3, wherein the identified optimum cuff pressure and/or volume is selected as a value corresponding to a target range between 30% to 50% of an overall compliance change in calculated cuff compliance to the physiological uniqueness of the given tracheal airway.

6. The device of claim 3, wherein automatically identifying the optimum cuff pressure and/or volume comprises (I) identifying three phases of compliance change associated with a respective tracheal airway compliance zone that include (i) a first phase in which an increase in compliance starting from a deflated state of the cuff is attributed to compliance of the cuff in a free space corresponding to a tracheal lumen, (ii) a second phase, subsequent to the first phase, in which a further change in compliance of the cuff is attributed to compliance via a direct interaction between the cuff and a tracheal mucosa layer, and a third phase, subsequent to the second phase, in which a still further change in compliance of the cuff is attributed to compliance via the cuff overcoming the tracheal mucosa layer and being impeded by a rigid tracheal cartilage structure, and (II) selecting, in response to identifying an end of the second phase, the optimum cuff pressure and/or volume as a value corresponding to between 30% to 50% of an overall compliance change within the second phase.

7. The device of claim 1, wherein the calculated cuff compliance includes a change in cuff compliance, wherein the change in cuff compliance is determined by a change in volume of the cuff divided by a corresponding change in cuff pressure.

8. The device of claim 1, wherein the calculated cuff compliance includes a change in total cuff compliance that comprises three components influenced by an anatomy of a trachea, each associated with a respective tracheal airway compliance zone, that includes (i) a tracheal lumen, (ii) a tracheal mucosa, and (iii) a tracheal cartilage.

9. The device of claim 8, wherein a first component comprises a compliance change in the tracheal lumen, C(TL), that corresponds with an actual compliance change of the cuff without any influence by a wall structure of the trachea,
wherein a second component comprises a compliance change in the tracheal mucosa, C(TM), that corresponds with an actual compliance change of the cuff with an influence of soft tissue of tracheal mucosa in response to the cuff contacting a surface of the tracheal mucosa,
wherein a third component comprises a compliance change in the tracheal cartilage, C(TC), that corresponds with an actual compliance change of the cuff with an influence of tracheal cartilage structure in response to the cuff overcoming the tracheal mucosa layer and becoming impeded by the structure of the tracheal cartilage, and
wherein the total cuff compliance, C(TOTAL), of the cuff in the tracheal airway is determined according to the equation:

$$1/(C(TOTAL))=1/(C(TL))+1/(C(TM))+1/(C(TC)).$$

10. The device of claim 1, wherein the volume-displacement subsystem (36) comprises a stepper motor with a fixed cylinder and linear plunger.

11. The device of claim 1, wherein the volume-displacement subsystem (36) comprises a centrifugal blower with a flowmeter and a flow control valve.

12. The device of claim 1, wherein the volume-displacement subsystem (36) is further configured for (i) inflating the cuff (90) for an intubation procedure and (ii) deflating the cuff for an extubation procedure.

13. The device of claim 1, wherein the compliance determination circuit (34) is further configured to calculate an overall compliance change as a function of the cuff and a given tracheal airway, wherein a default maximum allowable cuff pressure comprises 80% of the overall compliance change, the device further comprising:
a pressure relief valve (46) configured to activate, in response to a cuff overpressure condition, for connecting an outlet port of the cuff to atmosphere and dissipating the overpressure condition.

14. The device of claim 13, further comprising:
an alarm, wherein the cuff pressure controller (24) is further configured, responsive to an activation of the pressure relief valve (46), for activating the alarm, wherein the alarm comprises at least one of an auditory, visual, and tactile alarm.

15. The device of claim 1, further comprising:
an extubation assist feature, wherein the cuff pressure controller (24) is further configured, responsive to an initiation of the extubation assist feature, for precisely deflating, via the volume-displacement subsystem (36), an entire volume of pressurized gas from the cuff.

16. A ventilator system (580) for delivering pressurized gas to a tracheal airway, comprising:
a cuff pressure management device (10) according to claim 1, wherein the cuff pressure management device further comprises a cuff inflation/deflation connector (52) fluidly coupled to the volume displacement system (36); and
a ventilator source of pressurized gas (58) having a pressurized gas output, wherein the pressurized gas output is configured for being fluidly coupled to a breathing tube (54),
wherein the breathing tube comprises a length of tubing (92) with a ventilator connector (94) at a first proximal end and an atraumatic curved edge (96) at a distal end, wherein the breathing tube further comprises an inflatable cuff (90) proximate the distal end fluidly coupled to a cuff inflating tube (98), and
wherein the cuff inflation/deflation connector is configured to be fluidly coupled with the cuff inflating tube.

17. A method of cuff pressure management for a tracheal breathing tube with an inflatable cuff, comprising:
providing, via a volume displacement subsystem, (i) a measured volume of pressurized gas to and from the cuff and (ii) a cuff gas volume signal;
providing, via a pressure transducer, a cuff gas pressure signal;
calculating, via a compliance determination circuit, a cuff compliance based on the gas volume signal and the gas pressure signal;
determining a tracheal airway compliance zone based on the calculated cuff compliance; and
controlling, via a cuff pressure controller in controlling communication with the volume displacement subsystem and the compliance determination circuit, to maintain cuff pressure based on the calculated cuff compliance and the tracheal airway compliance zone.

18. The method of claim 17, further comprising:
automatically identifying, via the compliance determination circuit, an optimum cuff pressure and/or volume that is ideal to a physiological uniqueness of a given tracheal airway as a function of cuff compliance changes, wherein the optimum cuff pressure and/or volume to create an adequate seal to the physiological uniqueness in the given tracheal airway can vary over time, further wherein automatically identifying the optimum cuff pressure and/or volume comprises (I) identifying three phases of compliance change associated with a respective tracheal airway compliance zone that include (i) a first phase in which an increase in compliance starting from a deflated state of the cuff is attributed to compliance of the cuff in a free space corresponding to a tracheal lumen, (ii) a second phase, subsequent to the first phase, in which a further change in compliance of the cuff is attributed to compliance via a direct interaction between the cuff and a tracheal mucosa layer, and a third phase, subsequent to the second phase, in which a still further change in compliance of the cuff is attributed to compliance via the cuff overcoming the tracheal mucosa layer and being impeded by a rigid tracheal cartilage structure, and (II) selecting, in response to identifying an end of the second phase, the optimum cuff pressure and/or volume as a value corresponding to between 30% to 50% of an overall compliance change within the second phase.

19. The method of claim 17, wherein the calculated cuff compliance includes a change in total cuff compliance that comprises three components influenced by an anatomy of a trachea, each associated with a respective tracheal airway compliance zone, that includes (i) a tracheal lumen, (ii) a tracheal mucosa, and (iii) a tracheal cartilage.

20. The method of claim 19, wherein a first component comprises a compliance change in the tracheal lumen, C(TL), that corresponds with an actual compliance change of the cuff without any influence by a wall structure of the trachea, wherein a second component comprises a compliance change in the tracheal mucosa, C(TM), that corresponds with an actual compliance change of the cuff with an influence of soft tissue of tracheal mucosa in response to the cuff contacting a surface of the tracheal mucosa, wherein a third component comprises a compliance change in the tracheal cartilage, C(TC), that corresponds with an actual compliance change of the cuff with an influence of tracheal cartilage structure in response to the cuff overcoming the tracheal mucosa layer and becoming impeded by the structure of the tracheal cartilage, and wherein the total cuff compliance, C(TOTAL), of the cuff in the tracheal airway is determined according to the equation:

$$1/(C(TOTAL)) = 1/(C(TL)) + 1/(C(TM)) + 1/(C(TC)).$$

\* \* \* \* \*